United States Patent [19]

Eustache

[11] 4,042,575
[45] Aug. 16, 1977

[54] EXTRACTION OF GLYCOPROTEINS AND SIALIC ACID FROM WHEY

[75] Inventor: Jean-Marie Eustache, Martinvast, France

[73] Assignee: Union Cooperative Agricole Laitiere de la Manche, Sottevast, Brix, France

[21] Appl. No.: 624,305

[22] Filed: Oct. 20, 1975

[30] Foreign Application Priority Data

Oct. 22, 1974 France .................................. 74.35495

[51] Int. Cl.$^2$ ........................ A23J 1/20; B01D 13/00; C07G 7/00
[52] U.S. Cl. .............................. 260/112 R; 210/23 F; 426/583
[58] Field of Search ................... 260/112 R; 210/23 F, 210/321 R; 426/583

[56] References Cited

U.S. PATENT DOCUMENTS

| 3,583,968 | 6/1971 | Pien | 260/112 R |
| 3,947,598 | 3/1976 | Stenne | 210/23 F |

OTHER PUBLICATIONS

Whitehouse et al.–Methods of Biochem. Analysis (Wiley) (N.Y.) (1960), vol. VIII, 199–220.
Michaels–Chem. Eng. Progress 64 (No. 12), 31–43 (1968).
Porter et al.–Chem. Tech., pp. 56–63 (Jan. 1971).

Primary Examiner—Melvyn I. Marquis
Assistant Examiner—H. H. Fletcher
Attorney, Agent, or Firm—Synnestvedt & Lechner

[57] ABSTRACT

Process for the treatment of dairy or casein factory whey, notably for the extraction of glycoproteins and sialic acid.

The process includes ultrafiltration of casein whey, thermal flocculation of the proteins of the ultrafiltration retentate, phosphotungstic treatment of the supernatent obtained from the flocculation step, acid hydrolysis of the precipitate and treatment of the hydrolysis supernatent for the extraction of N-acetyl neuraminic acid (NANA).

34 Claims, 1 Drawing Figure

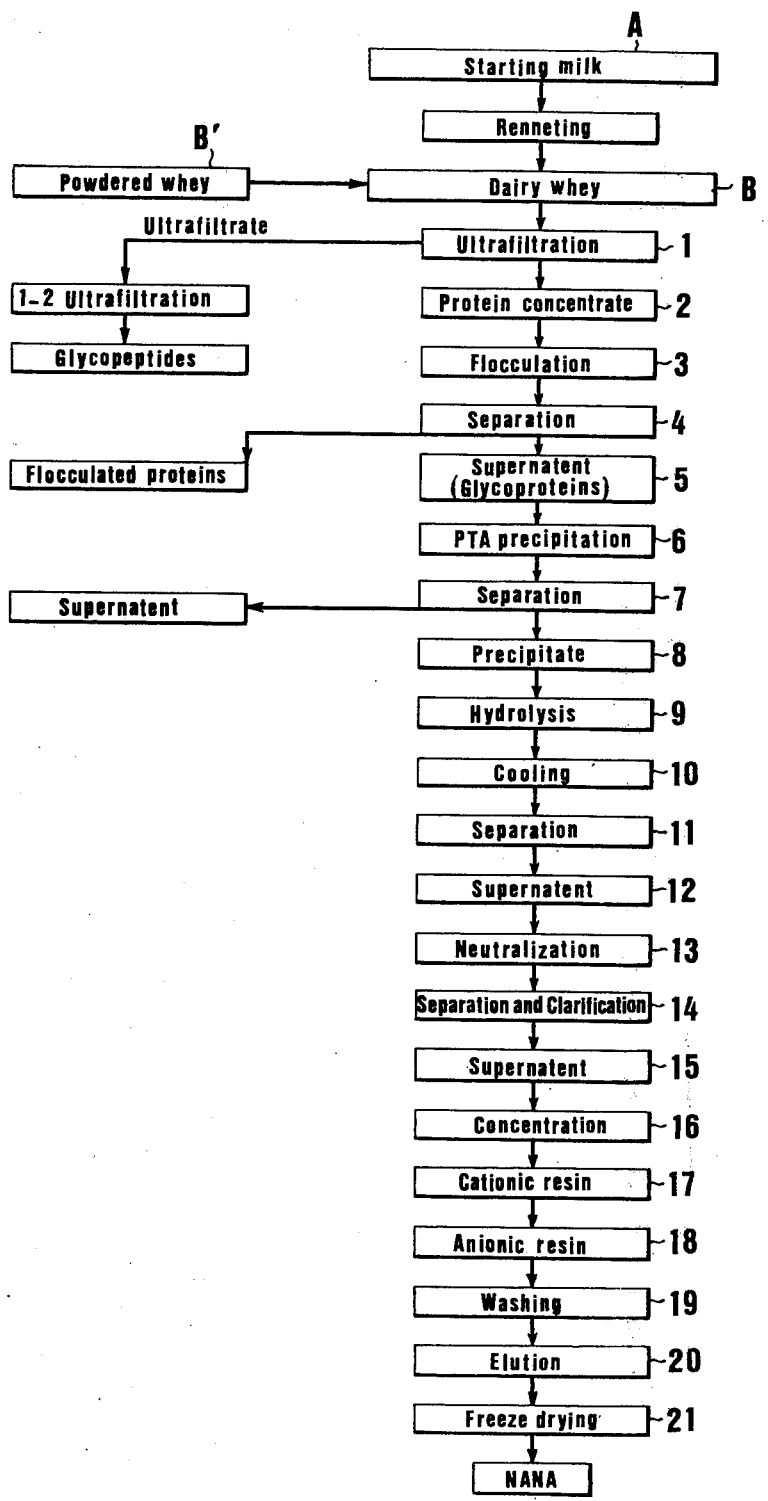

EXTRACTION OF GLYCOPROTEINS AND SIALIC ACID FROM WHEY

SUMMARY OF INVENTION

Generally speaking, the invention relates to the treatment of dairy or casein factory whey, Its object is more particularly a process permitting the extraction of glycoproteins and/or sialic acid from such a whey.

It is known that dairy whey is a yellowish liquid which, after its fat content has been removed by centrifugation, consistss mainly of lactose, proteins and mineral salts.

Treatments have already been proposed for dairy whey in order to render it non-polluting and to recover the proteins it contains. Large amounts of whey are produced by dairies and cheese factories, dairy whey being produced from milk after enzyme treatment and after traditional rennetting. It has thus been suggested that the proteins should be separated from the whey by ultrafiltration.

However, up to now, ultrafiltration has not been used for separating and obtaining certain specific proteins or other compounds which are of great interest in themselves.

This is notably the case of sialic acid, also called neuraminic acid (see, for example, MERCK Index, 7th Edition, p. 715). It is known that sialic acid is present in animal carbohydrate-protein complexes. In actual fact, this compound is at present prepared either from natural raw materials such as the sub-maxillary glands of bovines, or eggs, or by synthesis.

A bibliographical reference in this connection is the article by M. W. WHITEHOUSE and F. ZILLIKEN "Isolation and Determination of Neuraminic(sialic) acids", p.199 to 220 in "Methods of Biochemical analysis", Volume VIII (1960) Interscience, John Wiley Sons.

These known processes for the preparation of sialic acid are extremely costly, the cost of which is passed on to the market price of the product.

Bibliographical references for certain applications of sialic acid, and particularly of NANA include:
- "Coagulation of milk with rennet: Scientific and technical aspects" GARNIER, MOCQUOT, RIBADEAU-DUMAS,MAUBOIS-Ann de Nutrition Alimentaire, 1968, 22, B 495 - B 552.
- Svennerholm L. Acta Soc. Med. Upsaliensis, 61, 75 (1956) Arkiv. Kemi., 10, 577 (1956)
- Warren L. J. Biol. Chem. 233, 1971 (1959)
- Werner I. and L. ODIN, Acto Soc. Med. Upsaliensis 57, 230 (1952)
- Aminoff, D. (1961) Biochem J. 8L, 384 "The sensitivity of the Neuraminosidic Linkage in Muco-substances towards Acid and towards Neuraminidase Gibbons". Biochemistry Journal (1963) 89, 380.
- "Structure studies on the Myxovirus Hemagglutination Inhibitor of Human Erythrocytes". Ralph H. Kathan and Richard J. Winzler. Journal of Biological Chemistry (1963) vol. 238 N°1 p.21
- "Studies on the Neuraminidase of Influenza virus II additional properties of the enzymes from the Asian and PR 8 strains". Max E. Rafelson, J. R. Michael Schneir and Wannie W. Wilson, J. R. Archives of Biochemistry and Biophysics 103 (1963) 424- 430.

Other possible uses of sialic acid are given in the literature relating to this compound.

In another connection, it is advantageous to be able to obtain glycoproteins for use in cosmetic compositions.

An object of the present invention is a process for the treatment of dairy whey which makes it possible to obtain sialic acid very cheaply, and more specifically N-acetyl neuraminic acid (abbreviated to NANA) jointly with glycopeptides and a protein fraction consisting of glycoproteins.

DESCRIPTION OF DRAWINGS

The FIG. is a flow diagram of the process.

DETAILED DESCRIPTION

The invention relates to a process for the treatment of dairy whey, notably for the extraction of glycoproteins, glycopeptides and sialic acid, with ultrafiltration of said whey, characterized by the steps of a. ultrafiltration of dairy whey on membranes having a cut-off of from about 10,000 to about 50,000 in molecular weight providing an ultrafiltrate containing essentially lactose, mineral salts and glycopeptides, and a retentate containing proteins comprising, among other things, sialic acid; b. flocculation of the proteins of said retentate, resulting in a first protein precipitate and a first supernatent, which is separated and recovered; c. treatment of the first supernatent with phosphotungstic acid under conditions capable of forming a second supernatent and a second protein precipitate, which is separated and recovered; d. hydrolysis of the second precipitate, resulting in a third precipitate and a third supernatent, which is separated and recovered; e. further treatment of said third supernatent to extract the sialic acid contained therein, by known steps, comprising essentially the steps of neutralization, passing the last supernatent over catonic resin, fixing the sialic acid by passing over anionic resin, elution of the acid so fixed and recovery of an extremely pure sialic acid which can be freeze-dried.

As raw material for the process of the invention, dairy or casein factory whey is used which may be obtained from all ruminants' milk (cows, goats, ewes, buffalos and the like), notably obtained after enzymatic conversion, notably after cows or ewes milk has been rennetted. It is also possible to use dehydrated dairy or casein factory whey, as is usual during its conservation, the dry product having water added to it before its use in the process for reconstituting a liquid whey.

In step "a", the dairy or casein factory whey is subjected to ultrafiltration on membranes having an average cut-off expressed in molecular weight of between about 10,000 and about 50,000. With this in view, all types of membranes now available on the market or which can fulfill the above-mentioned conditions may be used. Organic or inorganic membranes may be used, including ceramic or metallic screens. Such membranes allow the lactose molecules, mineral salts and glycopeptides to pass through and retain the proteins. For industrial requirements it is, in fact, advantageous to recover the ultrafiltrate in a further treatment.

The practical conditions of ultrafiltration are conventional and can be adapted by a man skilled in the art to each specific case. For example, the whey may be flowed at sufficient speed at right angles to the membrane and under a pressure in the range of 3 bars, the product contacted with the membrane being recycled until the protein content of the retentate is optimal, which enables the progress of ultrafiltration to be known. As an example, the membranes "IRIS 3042" made by the French firm RHONE POULENC, which have a cut-off of about 15,000, are used in the ultrafiltration modules also sold by the aforesaid firm.

It is also possible to use the "DIAFLO" membranes sold by the firm AMICON (USA), such as the membranes DIAFLO XN 50 (cut-off = 50,000), DIAFLO PM 30 (cut-off = 30,000) and DIAFLO PM 10 or UM (cut-off = 10,000). The man skilled in the art will find in the technical handbooks issued by the makers of these membranes all the necessary information concerning their structure and method of use.

During further treatment, the ultrafiltrate is advantageously subjected to another ultrafiltration with membranes having a cut-off in the range of about between 1000 and 5000, expressed in molecular weight, such as a cut-off of 4000 for instance. It is, for example, possible to use the membrane sold under the name DIAFLO UM 2 (cut-off = 1000).

This further ultrafiltration provides a retentate containing glycopeptide which is a valuable product as, for example, an additional nutrient for human and animal feeding. The retentate only needs to be concentrated to provide a syrup of glycopeptides usable in practice, and the ultrafiltrate obtained from said further ultrafiltration essentially comprises lactose which can also be recovered after concentration. It should, furthermore be noted that, instead of being recovered in the form of glycopeptides, the retentate can be subjected to a treatment for the extraction of sialic acid under conditions similar to those which will now be described.

The retentate obtained in step a contains sialic acid and, more specifically, NANA. Before subjecting the retentate to the following step b, it may be advantageous to adjust its protein concentration, which generally involves diluting the retentate with water until a dry matter content of approximately 10% is obtained.

During step b, selective denaturation of soluble proteins is carried out by thermal flocculation. The albumines and globulines are thus precipitated and the peptone proteases which are glycoproteins are retained in the supernatent. The conditions of this treatment involve heating to a temperature and for a time sufficient to obtain precipitation of the proteins other than the sialoglycoproteins.

Suitable thermal treatment conditions involve, for example, a temperature of about 95° C and a duration of about 30 minutes. if lower temperature are used, the duration of treatment should be correspondingly lengthened. There is thus obtained a precipitate of proteins which can be recovered and a supernatent containing NANA which is subjected to the following steps of the process. To facilitate separation, the product is cooled, for example to a temperature of 4° C, which is the normal temperature in a refrigerator. The supernatent and protein precipitate are then separated by any suitable means and preferably by centrifugation. The supernatent obtained in step "b" is then contacted with an agent capable of precipitating all the proteins which it still contains. Phosphotungstic acid is used for this purpose; trichloroacetic acid, the reagent known for the precipitation of proteins, is not suited to the requirements of the present process as it only precipitates a portion of the proteins in the supernatent. The conditions of phosphotungstic treatment are not crucial, but it is preferable to operate at ambient temperature. The operation may be effected in an acid medium, for example, in the presence of sulphuric acid. The concentration of phosphotungstic acid can also be determined by a preliminary trial. Notably, amounts of approximately 5 g of phosphotungstic acid per liter of supernatent are used, it being understood that larger amounts can be used but do not provide any advantages and cost more. Phosphotungstic treatment is effected for a time sufficiently long to obtain precipitation of the proteins in the supernatent. Under the conditions previously described, for example, this period of time lasts for a few minutes, for example, 5 minutes at 25° C.

Following treatment with phosphotungstic acid, the protein precipitate is separated from the supernatent by any suitable means, by centrifugation for example. The precipitate is thus recovered and the supernatent expelled. During step d the precipitate separated out in step c is hydrolyzed. Hydrolysis can be effected by the acidic, enzymatic or basic hydrolysis, but acid hydrolysis is preferably used. It is preferable to use sulphuric acid, or any other acid capable of forming easily precipitable salts after the subsequent neutralization step. Hydrochloric acid is less suitable for this as it provides chloride ions which are difficult to remove subsequently. Acid hydrolysis is advantageously effected at high temperatures, but which should not be higher than about 98° C. The step is, for example, carried out at about 90° C. The acid is used at a moderate concentration, notably at less than 0.5N and, for example, of 0.1 N. Hydrolysis is continued for a time sufficient for said hydrolysis to be complete; this is generally about one hour.

After cooling, the product subjected to hydrolysis provides a precipitate and a supernatent, which are separated by any conventional means, notably by centrifugation. Said precipitate is eliminated, whereas the supernatent is recovered The further treatment of said supernatent, corresponding to step e of the process, comprises a certain number of operations enabling the NANA to be extracted. At this stage of the treatment of dairy whey, the invention makes use of the known technique for obtaining sialic acid. The supernatent is first neutralized with a view to precipitating, in the form of insoluble salts, the free $SO_4^{--}$ ions still present in the supernatent. This step is advantageously effected by the addition of barium hydroxide in excess for precipitating the sulphate ions if hydrolysis was effected with sulphuric acid.

An excess of barium ions is used until there is obtained a pH approximating neutral. The precipitated salts thus formed, such as barium sulphate, are then removed and the supernatent is retained. This is optionally concentrated before being flowed through the resin columns. Cationic resin is used for the first flow through in order to demineralize the supernatent. For example, resins available on the market under the name "DOWEX" are used, such as type AG 50 WX 8 H +. After passing over the cationic resin, the product is caused to flow through an anionic column in order to fix the NANA. Suitably, the resin available on the market under the name of DOWEX type AG 1 × 8 formate is used. The NANA is then obtained from the said anionic resin after washing the column with distilled water by elution notably with formic acid such as 0.3M formic acid if an anionic resin in the formate form is used.

Finally, a solution is obtained which, by freeze drying, provides an extremely pure NANA power. The operations constituting treatment e can undergo variations. For example, after neutralization, separation of barium sulphate and clarification of the supernatent, the supernatent can be dried. The powder obtained is then subjected to solvent extraction, that is to say, it is mixed with a solvent or mixture of solvents in which NANA is soluble, such as ethanol or an ethanol-water mixture. The NANA extracted is then isolated by elimination of the solvent.

The drawing illustrates the succession of steps of the process of the invention in a practical form of embodiment. Insofar as the raw materials are concerned, the dairy whey B is obtained either by adding rennet to milk A, or from powdered whey B' rehydrated for this purpose. The succession of steps can be clearly followed on the drawing. It should be noted that after ultrafiltration 1, the ultrafiltrate obtained is subjected to a further ultrafiltration 1-2, the retentate of which contains glycopeptides, which are some of the products obtained by the process of the invention.

After step 4 (separaton) a supernatent containing glycoproteins is obtained, these are another valuable product.

In step 6, the abbreviaton PTA designates phosphotungstic acid. The last step of the process (freezedrying 21) provides NANA, which is another product sought and obtained by the invention.

The invention will now be illustrated by examples of embodiments of the process.

EXAMPLE 1

1000 liters of cows milk were renneted in the traditional manner and 900 liters of dairy whey were obtained. These 900 liters of whey were flowed through an ultrafiltration module put on the market by the firm RHONE POULENC and provided with an IRIS 3042 membrane having a cut-off of 15.000. The whey was introduced into the module at a pressure of 3 bars and a temmperature of about ambient temperature.

870 liters of ultrafiltrate containing glycopeptides were thus obtained. Said ultrafiltrate was placed in an ultrafilration module provided with a membrane having a cut-off of 3000. The retentate obtained from this other ultrafilration was concentrated, which enabled 3700 grams of a syrup to be obtained having a dry matter content of 30% consisting essentially of glycopeptides. The retentate obtained from the first ultrafiltration is a concentrate of proteins with a 20% dry matter content containing about 100 grams of NANA. The retentate was diluted until a level of 10% dry matter was obtained, the proteins then being flocculated by heating at 95° C for 30 seconds. The product was then cooled to 4° C, then centrifuged until there was obtained a supernatent having a volume equal to 60% of the initial volume, which represents about 50 grams of NANA. This supernatent was treated by the addition of phosphotungstic acid at a rate of 5 grammes per liter and the reaction was continued with stirring for 5 minutes at 25° C. The precipitate obtained was separated and the supernatent eliminated. The precipitate contained 22 grams of NANA.

This precipitate was subjected to acid hydrolysis with 0.1 N sulphuric acid for 60 minutes at a temperature of 90° C. To facilitate separation of the precipitate the product was cooled to 4° C and centrifugration was used to separate the precipitate from the supernatent. The precipitate was expelled and the treatment was continued with the supernatent which contained about 20 grams of NANA. This supernatent was then neutralized by the addition of a saturated aqueous solution of barium hydroxide until a neutral pH was obtained, which resulted in the precipitation of the excess sulphate ions in the form of barium sulphate. The solution was then clarified and the barium sulphate removed. The supernatent which was reserved contained 19 grammes of NANA. Said supernatent was concentrated, for example by reducing its volume by 4 to 6-fold, using a rotating evaporator with vacuum, at a temperature of 45° C, the pressure being from 20 to 30 Hg. In order to demineralize the concentrated solution so obtained, it was flowed through a cationic resin column available on the market under the name of DOWEX, type AG 50 WX 8H+. At the output of said column and in order to fix the NANA, the solution is flowed through an anionic resin column of the type DOWEX AG 1 × 8 formate. Double distilled water was then used to wash the column containing the anionic resin and the NANA was eliminated with 0.3 N formic acid. 70% of the NANA fixed on the anionic resin was thus recovered. Freeze drying of the formic solution provided 13 grams of extremely pure NANA powder.

The economic value of the process is proved by the amount of NANA produced.

EXAMPLE 2

The operation was conducted under conditions identical to those used in example 1, but starting with 1000 liters of ewes milk, the results were substantially equivalent.

EXAMPLE 3

The operation was conducted as in example 1 but starting with a liquid whey obtained by the regeneration of powdered whey, 50 kg of whey powder was used, diluted to provide 900 liters of liquid whey.

What we claim is:

1. A method for the treatment of dairy or casein factory whey comprising the steps of:
    a. ultrafiltering the whey through membranes having a cut-off of about 10,000 to about 50,000 in molecular weight, providing an ultrafiltrate comprising lactose, mineral salts and glycopeptides, and a retentate comprising proteins and sialic acid;
    b. flocculating the proteins of said retentate providing a first protein precipitate and a first supernatent, which is separated and recovered;
    c. treating the first supernatent with phosphotungstic acid under conditions capable of forming a second supernatent and a second protein precipitate, which is separated and recovered;
    d. hydrolyzing the second precipitate, providing a third precipitate and a third supernatent, which is separated and recovered;
    e. extracting sialic acid from said third supernatent.

2. A method according to claim 1 wherein said whey is obtained by renneting of ruminant milk.

3. A method according to claim 1 wherein the membranes are organic membranes.

4. A method according to claim 1 wherein during the ultrafiltration of step (a) the whey is flowed over the membrane under a pressure of about 3 bars until an optimal protein content of the retentate is obtained.

5. A method according to claim 4 wherein the ultrafiltrate obtained from step (a) is subjected to another ultrafiltration with membranes having a cut-off in the range of about 1000 to 5000 in molecular weight, providing a second retentate comprising glycopeptides and a second ultrafiltrate comprising lactose and mineral salts.

6. A method according to claim 5 wherein the second retentate is recovered to form a concentrate of glycpeptides.

7. A method according to claim 1 wherein before step (b), the retentate obtained in step (a) is diluted by the addition of water to adjust its protein concentration to approximately 10%.

8. A method according to claim 1 wherein during step (b), selective denaturation of the soluble proteins in the retentate is effected by thermal flocculation, the conditions of said flocculation involving heating to a temperature and for a length of time sufficient to obtain the precipitation of albumines and globulines without denaturing the peptone proteases.

9. A method according to claim 8, wherein the thermal treatment of the retentate is effected at about 95° C, for about 30 minutes.

10. A method according to claim 8 wherein the product of thermal flocculation is cooled to facilitate separation of the flocculate.

11. A method according to claim 1 wherein the phosphotungstic treatment is effected in an acidic medium.

12. A method according to claim 1 wherein approximately 5g of phosphotungstic acid per liter of the supernatent is used.

13. A method according to claim 1 wherein during step (d), the precipitate separated in step (c) is hydrolyzed.

14. A method according to claim 13 wherein an acidic hydrolysis step is effected with sulphuric acid, at a concentration lower than 0.5N.

15. A method according to claim 13 wherein hydrolysis is effected at a temperature not higher than 98° C.

16. A method according to claim 1 wherein during treatment (e), the supernatent is neutralized in order to precipitate the free acid ions in the form of salts by the addition of excess barium hydroxide.

17. A method according to claim 1 wherein, during treatment step (e the third supernatent is dried and the powder obtained is subjected to solvent extraction, by putting the said powder into intimate contact with a solvent in which the NANA is soluble.

18. A method according to claim 1 wherein step (e) comprises neutralizing said third supernatent, passing said supernatent over cationic resin, passing said supernatent over anionic resin to fix the sialic acid, eluting the fixed sialic acid and recovering a sialic acid solution.

19. A method according to claim 1 wherein said whey is obtained by reconstituting dehydrated whey.

20. A method according to claim 1 wherein the membranes are inorganic.

21. A method according to claim 20 wherein the membranes are ceramic.

22. A method according to claim 20 wherein the membranes are metallic.

23. A method according to claim 5 wherein said sialic acid is extracted from said second retentate by steps (b), (c), (d) and (e).

24. A method according to claim 8 wherein said peptone proteases include sialoglycoproteins.

25. A method according to claim 10 wherein the product is cooled to about 4° C.

26. A method according to claim 11 wherein the acid medium includes sulphuric acid.

27. A method according to claim 13 wherein the hydrolysis is effected by acidic hydrolysis.

28. A method according to claim 13 wherein the hydrolysis is effected by basic hydrolysis.

29. A method according to claim 13 wherein the hydrolysis is effected by enzymatic hydrolysis.

30. The method according to claim 15 wherein hydrolysis is effected at about 95° C.

31. A method according to claim 14 wherein the supernatent is neutralized with barium hydroxide to precipitate sulfate ions.

32. A method according to claim 18 wherein the anionic resin is in the formate form and elution is effected with formic acid to recover the N-acetyl neuraminic acid.

33. A method according to claim 17 wherein said solvent includes ethanol.

34. A method according to claim 17 wherein said solvent is an acetone-water mixture.

* * * * *